United States Patent
Oh et al.

(10) Patent No.: US 9,283,385 B2
(45) Date of Patent: Mar. 15, 2016

(54) SEATING APPARATUS FOR DIAGNOSIS AND TREATMENT OF DIAGNOSING AND CURING URINARY INCONTINENCE, ERECTILE DYSFUNCTION AND DEFECATION DISORDERS

(71) Applicant: Gi Bum Oh, Seoul (KR)

(72) Inventors: Gi Bum Oh, Seoul (KR); Kyung Il Kim, Busan (KR)

(73) Assignee: UK DO-I CO., LTD., Seoul (KR)

( * ) Notice: Subject to any disclaimer, the term of this patent is extended or adjusted under 35 U.S.C. 154(b) by 0 days.

(21) Appl. No.: 14/082,076

(22) Filed: Nov. 15, 2013

(65) Prior Publication Data

US 2015/0141881 A1    May 21, 2015

(51) Int. Cl.
*A61H 23/00* (2006.01)
*A61N 1/36* (2006.01)
*A61F 7/12* (2006.01)
*A61N 5/06* (2006.01)

(52) U.S. Cl.
CPC .............. *A61N 1/36007* (2013.01); *A61F 7/12* (2013.01); *A61H 23/00* (2013.01); *A61N 5/0603* (2013.01)

(58) Field of Classification Search
CPC ........... A63B 2225/50; A63B 2220/56; A63B 21/008; A63B 2225/62; A63B 23/0244; A63B 23/20; A61N 1/36014; A61N 1/36007; A61N 1/0452; A47K 13/24
USPC .......................... 600/29, 546, 587, 591, 593; 606/191–193, 197; 482/92, 111–112
See application file for complete search history.

(56) References Cited

U.S. PATENT DOCUMENTS

| | | | | |
|---|---|---|---|---|
| 5,516,188 | A  * | 5/1996 | Bruhnke et al. | 297/129 |
| 6,206,463 | B1 * | 3/2001 | Whigham | 297/129 |
| 7,338,417 | B2 * | 3/2008 | Kang | 482/148 |
| 2003/0220589 | A1 * | 11/2003 | Leivseth et al. | 600/591 |
| 2008/0139876 | A1 * | 6/2008 | Kim | 600/29 |
| 2009/0270963 | A1 * | 10/2009 | Pelger et al. | 607/138 |
| 2011/0015472 | A1 * | 1/2011 | Lee | 600/29 |
| 2014/0155954 | A1 * | 6/2014 | Lee | 607/48 |

* cited by examiner

*Primary Examiner* — Rene Towa
(74) *Attorney, Agent, or Firm* — Lucas & Mercanti, LLP

(57) ABSTRACT

The present invention relates to a seating apparatus for the diagnosis and treatment, and more particularly, to a seating apparatus for diagnosis and treatment of diagnosing and curing urinary incontinence, erectile dysfunction and defecation disorders which enables to diagnose symptoms of urinary incontinence, erectile dysfunction and defecation disorders by measuring contraction pressure and contraction duration of pelvic floor muscles, muscles of perineum and anal sphincters of a user, who puts on cloth while seated, simultaneously with curing symptoms of urinary incontinence, erectile dysfunction and defecation disorders throughout biofeedback exercise and training.

9 Claims, 10 Drawing Sheets

SEATING APPARATUS FOR DIAGNOSIS AND TREATMENT OF DIAGNOSING AND CURING URINARY INCONTINENCE, ERECTILE DYSFUNCTION AND DEFECATION DISORDERS

FIELD OF THE PRESENT INVENTION

The present invention relates to a seating apparatus for diagnosis and treatment, and more particularly, to a seating apparatus for diagnosis and treatment of diagnosing and curing urinary incontinence, erectile dysfunction and defecation disorders which enables to diagnose symptoms of urinary incontinence, erectile dysfunction and defecation disorders by measuring contraction pressure and contraction duration of pelvic floor muscles, muscles of perineum and anal sphincters of a user, who puts on cloth while seated, simultaneously with curing symptoms of urinary incontinence, erectile dysfunction and defecation disorders throughout biofeedback exercise and training.

BACKGROUND OF THE PRESENT INVENTION

Urinary incontinence is a control problem of bladder and urethral sphincter, wherein urethral pressure normally exceeds bladder pressure, resulting in involuntary leakage of urine. It can be defined as a syndrome which means more than urination, causing involuntary urination visibly and preventing social activities or sanitation.

Types of urinary incontinence are urge incontinence, stress incontinence, and mixed stress & urge incontinence.

Urge incontinence is caused by instability of detrusor muscle. While feeling the urge to urinate, urge incontinence is involuntarily generated because there is no power to stop and bear the flow of urine.

Stress incontinence comes from increased intra-abdominal pressure, wherein insufficient strength of urethral ligaments, bulbocavernous muscles, transverses perineimuscles and anal sphincters increase intra-abdominal pressure, resulting in leakage of urine, under 50 ml. There are various kinds of reasons for increasing intra-abdominal pressure, such as coughing, sneezing, laughing, bearing down, running, nose blowing, rough exercise, impatience, excited condition, going up stairs quickly, sudden uprising, etc.

Mixed stress & urge incontinence refers to urinary incontinence in combination of urge incontinence and stress incontinence, due to reduction in tensible force of stress incontinence and detrusor muscle.

Generally, urinary incontinence happens to women more than men. The number of employed women is increasing more and more, and aging population is rapidly going up. Therefore, urinary incontinence gives women severe damage in terms of mental, social and economical sides. First of all, as for economical aspects, according to a report in U.S.A. in 1989, expenses for urinary incontinence treatment exceeded $10 billion, larger than those for AIDS treatment. It implies that urinary incontinence causes many economical problems.

As for physical damage, external genitals get wet all the time, resulting in fungal infections and contact dermatitis. As for mental damage, anxiety, tension and shame are due to unpleasant odor, disrupting personal relations and social activities. Also, negative impacts on self concept and self esteem cause mental disorders such as depression or emotional alienation.

Moreover, it has been revealed that the excessive increase of pelvic structure due to pregnancy and delivery weakens contractile force of pelvic floor muscles (vagina muscles), causing erectile dysfunction and urinary incontinence. It was reported that 90 percent of people avoid sexual performance more than once because of urinary incontinence, and more than 80 percent of women with severe symptom keep away from sexual performance. Urinary incontinence is a formidable disease of disrupting marital relation as well as causing inconvenience in daily life.

Urinary incontinence is diagnosed by medical examination by interview, questionnaire, uroflometer, residual urine test, urodynamic study, cystoscopy, radiographic and ultrasonic inspection, micturition chart, pad inspection, perineometer, etc. Among them, the perineometer, foreign-made, is divided into manual (pump) operation and automatic operation, and measures symptoms of urinary incontinence and effects of exercise for strengthening pelvic floor muscles (Kegel exercise) by measuring contraction pressure and duration of pelvic floor muscles in hospitals and research facilities in colleges. However, it is the problem that the perineometer needs professional knowledge. Thus, it is difficult for people to operate the perineometer.

Urinary incontinence is cured by medications, surgery, nonsurgical method, etc. Medications include anticholinergic drugs, smooth muscle relaxants, tricyclic antidepressant, etc. And, types of surgery are Sling operation, Burch operation, TVT (Tension-free vaginal tape), collagen injection, balloon treatment, etc.

There are physiotherapy and behavior therapy in nonsurgical treatments. Physiotherapy has electrical stimulation, transcranial magnetic stimulation, vaginal cone, hyperthermia, magnetic stimulation, perineometer feedback, etc.

Among them, the electrical stimulation refers to a method for inducing passive muscle strengthening by applying electrical stimulation to pelvic floor muscles; and the transcranial magnetic stimulation refers to a method for passively contracting pelvic floor muscles with magnetic field. Behavior therapy refers to bladder training, Kegel exercise, biofeedback, etc.

Bladder training means manual expression of bladder urine on time. Kegel exercise indicates pelvic muscle training designed by Arnold Kegel in 1948, widely used in curing urinary incontinence and muscles by improving functions and strengthening of muscles throughout contraction of pelvic floor muscles. Since pelvic floor muscles (vagina muscles) are not often used, it is important to exercise muscles in the right way. When exercising pelvic floor muscles, abdominal or hip muscles besides pelvic muscles may be used and then, this causes increased abdominal pressure and worse urinary incontinence.

Biofeedback refers to physiological self regulation, which is one of behavior treatment based on learning through reinforcement, suggested by B. F. Skinner, wherein a patient realizes what he sees, hears and feels himself by detecting his physiological responses and converting them into visual, auditory and sensible signals.

In addition, erectile dysfunction is divided into symptoms of female and male. There are sexual desire disorder, sexual arousal disorder, orgasmic disorder and dyspareunia in female erectile dysfunction.

In addition, there are premature ejaculation, impotence, painful ejaculation, prostatic disease and hyposexuality in male erectile dysfunction.

First, premature ejaculation, one of male erectile dysfunction, has no medically certain definition, but it is defined that 50 percent of total sexual intercourse occurs when a man can not control ejaculation and expels semen soon before a female partner feels satisfaction. Generally, 40 percent of adult men have this symptom. Premature ejaculation is a prevalent sexual dysfunction in men, accounting for 60~70 percent of patients who visit urological department. Although there may be statistical differences, it often occurs among high educational people and city dwellers. Recently, it is rapidly increasing among the young.

The main reason for premature ejaculation may have been considered as mental problems, but the exact reason has not been disclosed. Mental conflicts, worries, early sex activity, coitus interrupts by concern for pregnancy, masturbation, and abnormal feeling of glans may be the reasons. These can be diagnosed by self approach to sexual function, behavioral approach, psychological approach, medical examination by interview, physical examination, biothesiometry, penile color Doppler ultrasound, Rigiscan and ejaculatory duct sensitivity test.

The treatments of premature ejaculation are behavior therapy, medications, local application method, self injection for blood vessel expansion, penile dorsal neurectomy, autogenous dermis graft, transcranial magnetic stimulation of inside and outside of body, anal sphincters biofeedback therapy, oriental medicine and oriental suppository.

Next, impotence is defined as inability to develop or maintain an erection of the penis during sexual performance. 52 percent of adult men, over 40s, suffer from this symptom. The reasons are mental problems, aging, diseases, drug side effects, alcohol and smoking.

Impotence is diagnosed by medical history, medical examination by interview, International Index of Erectile Function (IIEF), physical examination, hormone examination, penile erection induction reaction test, transrectal ultrasonography, penile color Doppler ultrasound, dynamic infusion cavernosometry and cavernosography, penile arteriography, Rigiscan, snap gauge, visual stimulation examination and electromyography. Also, the treatments of impotence include psychiatric therapy, medications, penile vascular surgery, penile vascular reconstructive surgery, penile vein ligation for venogenic impotence, penile prosthesis, self injection for blood vessel expansion, penile vacuum constriction device, transcranial magnetic stimulation of inside and outside of body, anal sphincters biofeedback therapy, oriental medicine and oriental suppository.

Next, there is sexual disorder which comes from prostatic disease.

Located at the bottom face of bladder between pubic bones and rectum, prostate is fixed to bladder neck, on the top, urogenital diaphoretic, at the low side, and puboprostatic ligament in front, and is deeply situated in pelvic cavity. It is an approximately 20-gram chestnut-shaped organ surrounding posterior urethra in a form of wheels, and is a sex organ only existed in males. Urethra is obliquely penetrating toward the front side of the prostate. Also, both ejaculatory ducts are passing through parenchyma at the back of the urethra. Divided into three glandular lobes, the parenchyma of the prostate is composed of tract vesicular structures whose types are glandular tissue and interstitium, wherein a middle lobe is upper than a penetrated part of the ejaculatory ducts and a side lobe is in the right and left of the urethra. In addition, the prostate provides sperm in testicle with nutrition by producing 30 percent of semen and helps fertility of sperm throughout liquefying ejaculated semen and reinforcing sperm motility. Also, alkaline prostatic fluid has an important role in sperm, namely, helping sperm to reach to oviduct for fertilization throughout neutralizing the inside of strong acid vagina.

Meanwhile, diseases related to the prostate are classified into prostatitis, prostatomegaly and prostate cancer. Among prostate diseases, prostatitis mostly occurs in Koreans more than Westerners and the frequency of prostate cancer is relatively low. However, the frequency of prostatomegaly and prostate cancer has been gradually increased due to western lifestyle and the increase of aging population.

First, prostatitis is inflammation of the prostate. 30 percent of men in their 20s to 50s suffer from the prostatitis; 50 percent of men experience once in their lives; and this is the most common disease that 25 percent of patients who visit urological department suffer from. There are acute and chronic bacterial prostatitis, chronic noninfectious prostatitis and prostatodynia.

Symptoms of prostatitis are micturition disorders, such as residual urine, urinary frequency, nocturia, pyuria and narrow voiding stream, and male erectile dysfunctions, such as unpleasant feeling and pain in lower abdomen and perineum, backache, didymalgia, dysuria, whole muscle pain, painful ejaculation, premature ejaculation and impotence.

Further, prostatitis is diagnosed by papation test, inflammatory cell test, bacterial culture, uroflowmetry test, cystoscope test, prostate ultrasonography, color Doppler ultrasound, and polymerase chain reaction (PCR) test. Treatments of prostatitis include special antibiotics, anticholinergic drugs, alpha blocker, hormone drugs, skeletal muscle relaxants, medicine injection into prostate, neurodepressive therapy, microwave thermotherapy, sacral nerve stimulation, transurethral needle ablation (TUNA), oriental medicine, oriental suppository, anti-inflammatory analgesic drug, prostate massage, sitz bath in warm water, thermal massage, low frequency electrical stimulation, transcranial magnetic stimulation of inside and outside of body, biofeedback exercise, pelvic exercise and diet therapy.

However, prostatitis is considered as a chronic disease because it is often hard to find out causative organisms and reasons for prostatitis; there is a limit (about 60 percent, cured) to cure with medicine due to no medicinal penetration of prostate, consisting of special cells; and it is frequently recurred even after symptoms are alleviated. Accordingly, since many patients long for treatment in various ways, not only the efficiency of occupation is declined due to physical, economical and mental exhaustion, but the quality of life is remarkably endangered.

Next, prostatic hypertrophy, most common in prostate of men after middle age, is a disease which causes defecation disorders and erectile dysfunction. It is occurred by multiplying epitheliums, smooth muscles and connective tissue of prostate in terms of histology, and urinary tract is pressurized by enlarged prostate and uroflow resistance in terms of functions. Also, genetic factors, physical constitution, nutrition, artery hardening and differences among human races are considered as the causes of prostatic hypertrophy, but these have not been correctly revealed. Given high frequency among old people, it is closely related to male hormones.

Treatments of prostatic hypertrophy include medical history, International Prostate Symptoms Score (I-PSS), digital rectal examination, uroflometer, residual urine test, transrectal ultrasonography, tissue inspection, prostate specific antigen (PSA), bladder scan, urine examination, tissue inspection and renal function test. Symptoms of prostatic hypertrophy are defecation disorders, such as urinary frequency, nycturia, hesitancy, pyuria, residual urine and retention of urine, and male erectile dysfunctions, such as unpleasant feeling and pain in lower abdomen and perineum, backache, didymalgia, dysuria, whole muscle pain, painful ejaculation, premature ejaculation and impotence. Treatments of prostatic hypertrophy are classified into watchful waiting, medical treatment, physical treatment, minimaly invasive therapy, and surgical treatment: there are alpha-adrenergic antagonists, Finasteride, anti-androgens, oriental medicine and oriental suppository in medical treatment; there are biofeedback therapy, low frequency electrical stimulation and transcranial magnetic stimulation of inside and outside of body in physical treatment; there are ballon dilatation, prostate stents, thermotherapy (TUMT), TULIP, VLAP, TUEP, KTP, high intensity focused ultrasound (HIFU), transurethral needle ablation (TUNA), laser prostatectomy, electro vaporization and thermal therapy in minimaly invasive therapy; and there are transurethral resection of prostate (TURP), transurethral incision of prostate (TUIP) and open prostatectomy in surgical treatment.

Next, prostatic carcinoma refers to a malignant tumor which starts from surrounding areas of prostate. It frequently occurs as long as people get older: men over 50 mostly develop prostatic carcinoma. It is a quite common disease in Westerners, especially in men, and prostatic carcinoma is the second highest death rates after lung cancer. The frequency of prostatic carcinoma in Korean men is lower than that of Westerners, but aging population is steadily increasing due to Westernized food style, air pollution, environment pollution, etc.

In addition, it is reported that genetic factors, age and male hormones are assumed as the causes of prostatic carcinoma even though these causes seem uncertain. Prostatic carcinoma starts gradually, thus unrecognized. At first, unpleasant feeling and pain in perineal region and rectum occur. Then, defecation disorders, hematuria, pyuria, and renal dysfunction are shown gradually. Metastasis mostly occurs in bones. Prostatic carcinoma is accidentally found during annual medical checkup or prostate hypertrophy examination rather than a patient or a doctor's concern and conscious symptoms.

Prostatic carcinoma is diagnosed by Digital Rectal Examination (DRE), transrectal ultrasonography, tissue examination, Prostate Specific Antigen (PSA) test, perineal punch biopsy, bone scan, and lymphangiography. Treatments of prostatic carcinoma include hormonal therapy for medicating antiandrogen or female hormones; surgical therapy for performing radical prostatectomy; radio therapy for applying radiation to external affected prostate; and Chemo therapy for medicating more than two anticancer drugs when hormone therapy is not valid. The prognosis of prostatic carcinoma depends on physical condition, age, and character (differentiated degree) of cancer cells. Generally, the progress of prostatic carcinoma is slow. Thus, five year survival rates are 70~90 percent when cancer is limited to prostate; 50~70 percent when cancer spreads to the surroundings of prostate; 30~50 percent when cancer spreads to lymph node; and 20~30 percent for remote metastasis to bones or lung. Also, five year survival rates are 85~95 percent for radical prostatectomy.

Meanwhile, brief explanations on "hemorrhoids (haemorrhoids)", "fecal incontinence", and "constipation", which are major symptoms of defecation disorders, are as follows.

First, most of adult suffer from hemorrhoids, which is a disease occurring in the bottom of rectum, anus, and tissue of the surrounding of anus. Types include haemorrhoids, anal fistula, anal fissure, anusitis, pruritus ani, and rectal prolapse.

Among them, "haemorrhoids", which accounts for 50 percent and is mostly recognized as hemorrhoids, is a disease in which interior blood vessels of anus are expanded for some reasons, thus making anal mucosal surfaces, which cover the blood vessels, abnormally enlarged or stretched and even protruded outside the anus in severe cases. 40~50 percent of adult men and women suffer from haemorrhoids. It is classified into internal hemorrhoids (20 percent), external hemorrhoids (10 percent) and mixed hemorrhoids in accordance with shapes and positions, and it is generated by aging, genetic factors, abnormal defecation habit such as constipation and diarrhea, wrong food life like eating meat and drinking alcohol, overwork, physical fatigue, hepatocirrhosis, tumors in abdominal cavity, and pregnancy. Types of diagnosis include medical examination by interview, inspection, Digital Rectal Examination (DRE), proctoscope, sigmoidoscopy, anorectal ultrasonography, anorectal manometry, and anal electromyography.

Treatments of hemorrhoids are diet therapy, exercise, sitz bath in warm water, massage, ointment, suppository, thermal therapy, oriental medicine, oriental suppository, biofeedback therapy, injection, elastic ring ligature, infrared heat photocoagulation, cryotherapy, laser treatment, and surgery.

Next, fecal incontinence means excretion of gas or liquid excrement in unconscious state. This is not a disease, but a symptom which influences patients' lives by causing severe mental anguish. It occurs for various reasons of damage of pelvic muscles, anal sphincters, central nerves and pudendal nerves, sense malfunction of rectum, dysfunction of anal sphincters, congenital malformation, childbirth, and long-time use of obstruent. Fecal incontinence is diagnosed by physical examination by interview, anorectal manometry, anal electromyography, defecography, and anal ultrasonography. Also, it is cured by diet therapy, medications, gastro-colic reflex, biofeedback therapy for rectum and anal sphincters, anal sphincters repair, and postanal redressement.

Next, constipation, a major symptom of defecation disorders, refers to a situation that the number of defecation is less than twice a week; the weigh of bowel movements is below 35 g a day; 25 percent from the total bowel movements go for hard stool or sensation of incomplete evacuation; and more than two symptoms among the above situations continue over 3 months. Frequency is about 10 percent of the total population: especially, the frequency of young women and old people is approximately three times higher than that of men or young people. Causes include: mental or environmental factors (stress), wrong food style, dyscrinism, disturbances of metabolism, nerve disorder, drug abuse, and constitutional abnormality of large intestine or anus. Constipation is diagnosed by digital rectal examination, colonoscopy, colonic transit time, large bowel study, endoanal ultrasonography, anal sphincters electromyography, and anal manometry. It is treated with bowel movements training, intake of dietary fiber and lactic acid bacteria, change of living habits, medications, oriental medicine, oriental suppository, biofeedback therapy for rectum and anal sphincters, low frequency electrical stimulation, transcranial magnetic stimulation of inside and outside of body, and surgery. Among these methods, "biofeedback therapy" refers to contraction and relaxation therapy which is now significantly effective in constipation and fecal incontinence. It treats symptoms by doing exercise in person while checking status of contraction and relaxation of one's rectum and anal sphincters through probe, LCD display and headphones, and strengthening functions of declined sense of rectum and sphincters with maximized capacity of somatic nerves, autonomic nerves and sensory motor neuron. This is the most fundamental and effective treatment among methods for curing constipation and fecal incontinence.

Explanations on causes, symptoms and treatments of urinary incontinence, erectile dysfunction, prostatic disease and defecation disorders are described as above. General explanations on biofeedback exercise and practical use are as follows.

Anorectal physiology examination of pelvic floor muscles (vagina muscles), muscles of perineum, and anal sphincters is a means for diagnosing urinary incontinence, erectile dysfunction, prostatic disease and defecation disorders: types include anorectal manometry, balloon expulsion test, balloon proctography, defecography, colonic transit time study, anal electromyography, transcrectal ultrasonography, anorectal angle, and saline continence test.

Further, among these types, the anorectal manometry is equipped with both physiologic test for rectum and anal sphincters and biofeedback therapy, widely used in hospitals in relation to large intestine and anus diseases.

In addition, biofeedback, a compound word of biology and feedback, refers to physiological self regulation, which is one of behavior treatment based on learning through reinforcement, suggested by B. F. Skinner, wherein a patient realizes what he sees, hears and feels himself by detecting his physiological responses and converting them into visual, auditory and sensible signals. Recently, it belongs to one of orthodox medicine across alternative medicine and complementary medicine, and it is widely utilized in curing more than about 150 symptoms. Biofeedback exercise is applied in pelvic floor muscle biofeedback exercise used in incontinence treatment, vagina muscle and anal sphincters biofeedback exercise used in erectile dysfunction treatment, rectum and anal sphincters biofeedback exercise used in irritable bowel syndrome, constipation, and fecal incontinence, frontal muscle electromyelogram (EMG) biofeedback exercise used in control of brainwave, electro cardiogram biofeedback exercise used in high blood pressure and arrhythmia treatment, body temperature biofeedback exercise, and Galvanic skin response biofeedback exercise.

As stated above, besides a means for diagnosing and curing urinary incontinence, erectile dysfunction, prostatic disease and defecation disorders, there are apparatus, currently used or granted for patent (utility model), such as a pole-shaped anus injecting apparatus using very low frequency (VLF), ultrasound, infrared ray, near infrared (NIR), laser, heat, warm water, vibration, and vacuum, urethra injection catheter using ultrasound, perineum massaging apparatus using vibration, heat, and low frequency, warm-water bath, sitz bath in warm water, and hot mugwort pipe shape using oriental medicine like mugwort.

However, such apparatuses just temporarily alleviate pain or unpleasant feeling. Also, the effect of treatment works in the short term, thus not satisfying users.

Furthermore, oral medication, used for treatment, has problems of side effects, like drug tolerance, organic malfunction and organic damage due to long-term drug taking, and should combine surgery because only medication can not completely cure diseases. As for western suppository and oriental suppository, effects do not last long. Not only is it very unhealthy because of finger-using injection into rectum and anus, but patients should live with long-time injection. Nevertheless, medications can not be fully absorbed into human body.

Also, anorectal manometry makes up the majority of physiologic test and biofeedback treatment for anal diseases, defecation disorders and erectile dysfunction and is used in most of hospitals. However, patients should visit hospital many times, and it is too complex to operate for users. Also, it is quite expensive and therefore, it costs a lot for inspection and treatment.

Furthermore, widely used in urinary incontinence and defecation disorders, low frequency electrical stimulation and transcranial magnetic stimulation of inside and outside of body use current and magnetic field, thus making contraction and relaxation of muscles move. Treatment effects are short; it may be recurred; and scientific reproducibility is not enough.

In addition, as for antibiotics widely used in prostate and anal diseases, there have been resistant bacteria which can not be cured by existing antibiotics: these have been incurred by misuse and overdose in advanced countries, and drug tolerance by small dose, below adequate amount, in developing countries. Thus, the World is currently facing to a serious level. Actually, in U.S.A., medical expenses for antibiotic tolerance amount for about $30 billion per year. In Korea, antibiotics consumption is about 33.2 people for every 1,000 people a day. It is 1.5 times higher than OECD (Organization of Economic Corporation and Development)'s average of 21.3 people. Also, the rate of prescription for antibiotics in hospitals is 58.9 percent, more than 2~3 times exceedingly higher than WHO (World Health Organization)'s recommended value of 22.7 percent; and the rate of prescription for injections amounts to 56.6 percent, even 3 times higher than WHO's recommended value of 17.2 percent. Especially, the resistant rate of penicillin for *staphylococcus* is 95 percent and thus, the rate of antibiotics misuse in Korea is the world's highest. The number of antibiotics resistant patients is on the increase, and efforts to stop this situation are just temporary solutions. Thus, now, there is no any special way.

Further, as for a personal apparatus for diagnosis and treatment using silicon air probe (Korean Patent nos. 10-0710908, 10-0727783), filed by the applicant of the present invention and granted for patent, a diagnosis and treatment apparatus for hospitals has a problem that a patient, who goes to a hospital for the first time, must inject an air probe into his coelom by nurse's assistance at a partially open place, thus causing inconvenience and shame, although it is rare for most of users to feel shame and inconvenience because of home use.

PRIOR ART

Reference

Korean Patent Registration No. 10-0710908
Korean Patent Registration No. 10-0727783

DISCLOSURE

Technical Problem

For solving above problems, the object of the present invention is to provide a seating apparatus for diagnosis and treatment of diagnosing and curing urinary incontinence, erectile dysfunction and defecation disorders which enables a nurse or a user to conveniently diagnose symptoms of urinary incontinence, erectile dysfunction and defecation disorders by easily measuring contraction pressure and contraction duration of pelvic floor muscles, muscles of perineum and anal sphincters by means of a seat-based contact probe sensor while a user puts on cloth, seated on the present apparatus in public place like hospital, and to conveniently and scientifically cure symptoms of urinary incontinence, erectile dysfunction and defecation disorders throughout biofeedback exercise and training.

Further, the other object of the present invention is to provide a seating apparatus for diagnosis and treatment of diagnosing and curing urinary incontinence, erectile dysfunction and defecation disorders which enables to diagnose symptoms of urinary incontinence and erectile dysfunction in person by injecting an implantable air probe sensor, connected to the main body, to coelom of a user who is seated on the present apparatus or lies in bed at a private place like home and more accurately and scientifically measuring contraction pressure and contraction duration of pelvic floor muscles (vagina muscles) and anal sphincters, and to cure symptoms of urinary incontinence, erectile dysfunction and defecation disorders throughout more accurate and scientific biofeedback exercise and training of pelvic floor muscles (vagina muscles) and anal sphincters.

Further, the other object of the present invention is to provide a seating apparatus for diagnosis and treatment of diagnosing and curing urinary incontinence, erectile dysfunction and defecation disorders which enables to diagnose symptoms of urinary incontinence and erectile dysfunction by injecting an implantable electric probe sensor to coelom of a user who is seated or lies in bed at a private place like home and measuring bio electrical impedance of pelvic floor muscles (vagina muscles) and anal sphincters, and to cure symptoms of urinary incontinence, erectile dysfunction and defecation disorders by applying electricity to pelvic floor muscles (vagina muscles) and anal sphincters.

Technical Solution

To accomplish above objects, the present invention relates to a seating apparatus for diagnosis and treatment of diagnosing and curing urinary incontinence, erectile dysfunction and defecation disorders comprising: a main case equipped with a space inside and shaped like an open-top hexahedron; a seat configured to connect to the upper side of the main case and to form a through hole in the center; a contact-type air probe sensor module configured to be fixed to the inside of the main case by penetrating the through hole of the seat to make the top protruded toward the upper side of the seat, to measure contraction pressure and duration of pelvic floor muscles, muscles of perineum and anal sphincters of a user while being moved up and down and expanded by air, and to induce contraction and relaxation; an air generation module, equipped with an air outlet to supply air to an external device, configured to be fixed to the inside of the main case and to supply air through the contact-type air probe sensor module; a control module configured to be fixed to the inside of the main case, to control each component in accordance with control instruction inputted from the outside, to measure contraction pressure and contraction duration of pelvic floor muscles (vagina muscles), muscles of perineum and anal sphincters for supplying these information toward outside in order to diagnose urinary incontinence, erectile dysfunction and defecation disorders by using an input value, measured from the air generation module, and to measure bio electrical impedance of pelvic floor muscles (vagina muscles) and anal sphincters on a basis of signals inputted from the external device for supplying these information toward outside; a power module, equipped with a power plug to the outer surface of the main case, configured to charge a battery in the main case with power source supplied from the power plug, to supply voltage, outputted from the battery, to each component, and to control intensity of electric current outputted from the battery in accordance with external control; an interface module, installed to the outer surface of the main case, configured to connect to the external device by electrically combining the control module and the power module; and a display module configured to display all data outputted from the control module and the external device by electrically connecting to the control module and the power module while accessing to the interface module, and to transfer the inputted control instruction to the control module.

Hereinafter, the external device is an implantable electric probe sensor configured to connect to the interface module, to be outputted by the control module with measured bio electrical impedance of pelvic floor muscles (vagina muscles) and anal sphincters of a user for diagnosing urinary incontinence and erectile dysfunction with power source of the power module, and to output current which enforces contraction and relaxation of pelvic floor muscles (vagina muscles) and anal sphincters of a user in accordance with regulation of the control module.

Hereinafter, the external device is an implantable air probe sensor configured to mechanically combine with the air outlet of the air generation module, to measure contraction pressure and contraction duration of pelvic floor muscles (vagina muscles) and anal sphincters of a user by being expanded by air while accessing to the interface module, and to induce contraction and relaxation.

Hereinafter, the main case, made up of synthetic resins or metal, comprises a handle in a front side, a support at the bottom, and a storage groove for storing the display module, the implantable electric probe sensor and the implantable air probe sensor to one side.

Hereinafter, the seat further includes a first heater installed inside; and a back combined to be folded in the rear of the main case.

Hereinafter, the contact-type air probe sensor module comprises: a frame, shaped like a "冂"-figured open-top cylinder, configured to form a rectangle's first air tube hole to the side; a lifting member, shaped like a "凵"-figured open-top cylinder, configured to form a second air tube hole to the side and to move up and down in the frame; an air bag, installed at the bottom of the lifting member in the frame, configured to be expanded by air, supplied from the air generation module, and to move up the lifting member; and a contact-type probe sensor, made up of transparent or translucent elastic material, configured to be the form of streamline for adhering to pelvic floor muscles, muscles of perineum and anal sphincters of a user upon expansion by air supplied from the air generation module, and to fix the bottom by means of the top of the lifting member and clamping rings.

Hereinafter, the contact-type air probe sensor module further includes: a first light source, installed inside of the lifting member, configured to investigate light; and a first vibration-generating motor, installed in one side of the lifting member, configured to generate vibration.

Hereinafter, the air generation module comprises: an air pump configured to generate air; a distribution terminal configured to distribute air generated from the air pump; an air blocking valve configured to connect to one side of the distribution terminal; a first air tube, made up of flexible material, configured to expand the contact-type probe sensor by penetrating the air tube hole formed in the air blocking valve and the frame of the contact-type air probe sensor module and combining to the second air tube hole of the lifting member; a second air tube, made up of flexible material, configured to expand the air bag by penetrating the first air tube hole formed in the air blocking valve and the frame of the contact-type air probe sensor module and combining to the air bag; a third air tube configured to combine the other side and one side of the distribution terminal; a fourth air tube configured to interconnecting the air blocking valve and the air outlet; and a pressure sensor configured to connect to the other side of the third air tube, and to output an input value by means of the control module with measured pressure which is electrically connected to the control module.

Hereinafter, the implantable electric probe sensor further includes a second heater configured to generate heat; a second light source configured to investigate light; and a second vibration-generating motor configured to generate vibration.

Hereinafter, the implantable air probe sensor further includes a third heater configured to generate heat; a third light source configured to investigate light; and a third vibration-generating motor configured to generate vibration.

Hereinafter, the control module further includes a first wireless communication equipment configured to transmit and receive the display module based on wireless data, and the display module further includes a second wireless communication equipment configured to transmit and receive the control module based on wireless data.

According to the seating apparatus for diagnosis and treatment of diagnosing and curing urinary incontinence, erectile dysfunction and defecation disorders of the present invention, as constituted above, it enables a nurse or a user to conveniently diagnose symptoms of urinary incontinence, erectile dysfunction and defecation disorders by easily measuring contraction pressure and contraction duration of pelvic floor muscles, muscles of perineum and anal sphincters by means of a seat-based contact probe sensor while a user puts on cloth, seated on the present apparatus in public place like hospital, and to conveniently and scientifically cure symptoms of urinary incontinence, erectile dysfunction and defecation disorders throughout biofeedback exercise and training.

Further, it enables to diagnose symptoms of urinary incontinence and erectile dysfunction in person by injecting an implantable air probe sensor, connected to the main body, to coelom of a user who is seated on the present apparatus or lies in bed at a private place like home and more accurately and scientifically measuring contraction pressure and contraction duration of pelvic floor muscles (vagina muscles) and anal sphincters, and to cure symptoms of urinary incontinence, erectile dysfunction and defecation disorders throughout more accurate and scientific biofeedback exercise and training of pelvic floor muscles (vagina muscles) and anal sphincters.

Further, it enables to diagnose symptoms of urinary incontinence and erectile dysfunction by injecting an implantable electric probe sensor to coelom of a user who is seated or lies in bed at a private place like home and measuring bio electrical impedance of pelvic floor muscles (vagina muscles) and anal sphincters, and to cure symptoms of urinary incontinence, erectile dysfunction and defecation disorders by applying electricity to pelvic floor muscles (vagina muscles) and anal sphincters.

DETAILED DESCRIPTION OF THE PREFERRED EMBODIMENT OF THE PRESENT INVENTION

The configuration of a seating apparatus for diagnosis and treatment of diagnosing and curing urinary incontinence, erectile dysfunction and defecation disorders, according to the present invention, will be described in detail with the accompanying drawing.

In the following description of the present invention, a detailed description of known incorporated functions and configurations will be omitted when to include them would make the subject matter of the present invention rather unclear. Also, the terms used in the following description are defined taking into consideration the functions provided in the present invention. The definitions of these terms should be determined based on the whole content of this specification, because they may be changed in accordance with the option of a user or operator or a usual practice.

Figure 1:
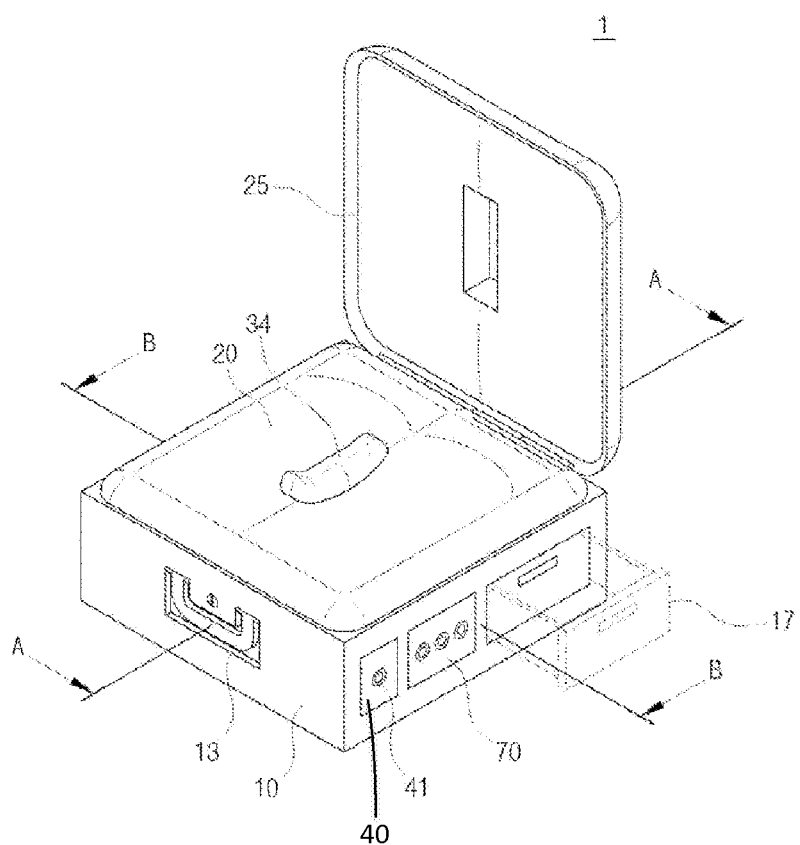
FIG. 1 illustrates a perspective diagram showing the constitution of a seating apparatus for diagnosis and treatment of diagnosing and curing urinary incontinence, erectile dysfunction and defecation disorders according to the present invention.
Figure 2:
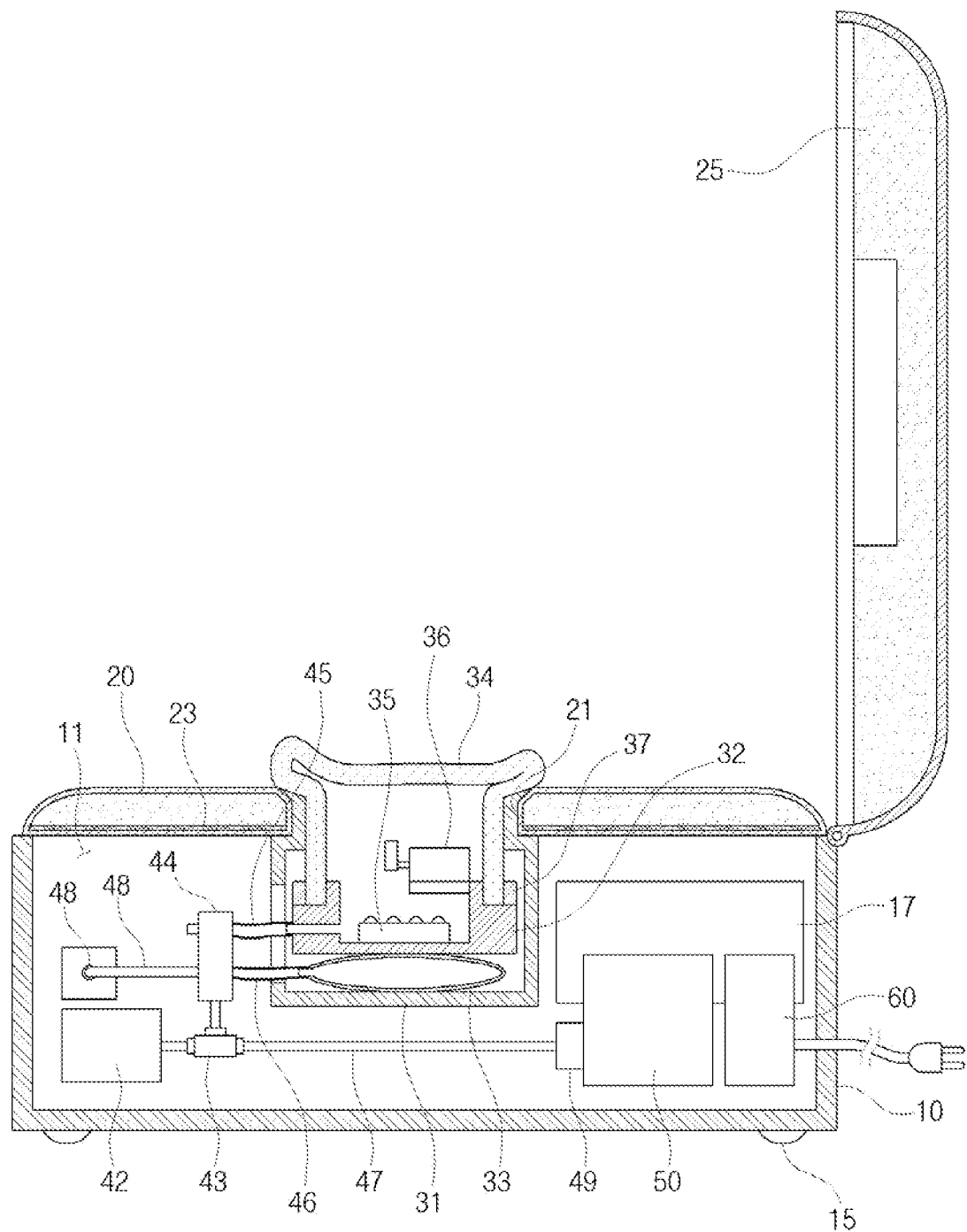
FIG. 2 illustrates a sectional diagram A-A of FIG. 1.
Figure 3:
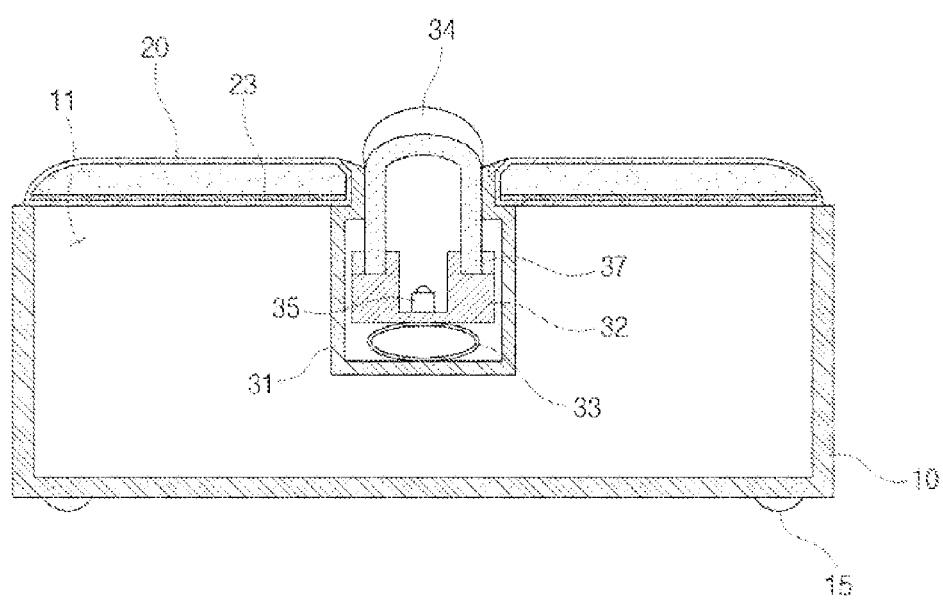
FIG. 3 illustrates a sectional diagram B-B of FIG. 1.
Figure 4:
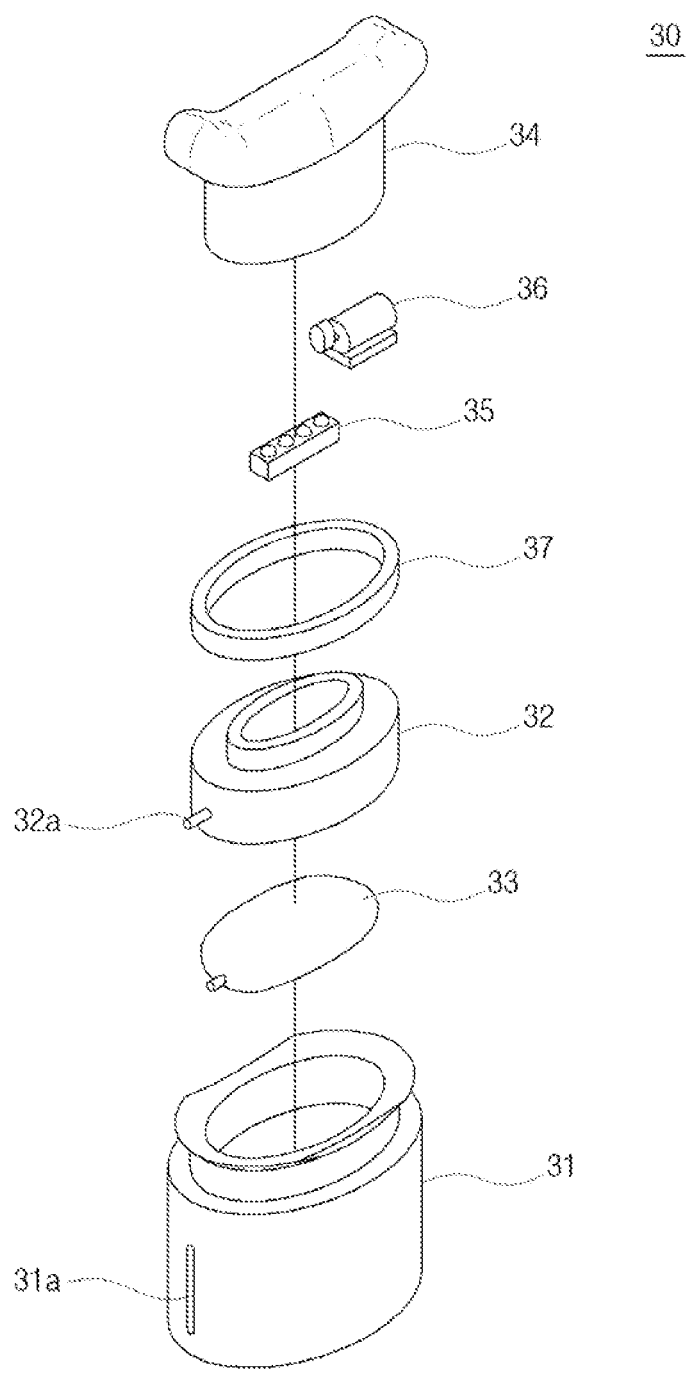
FIG. 4 illustrates an exploded perspective diagram of the constitution of a contact-type air probe sensor module of the seating apparatus for diagnosis and treatment of diagnosing and curing urinary incontinence, erectile dysfunction and defecation disorders according to the present invention.
Figure 5:
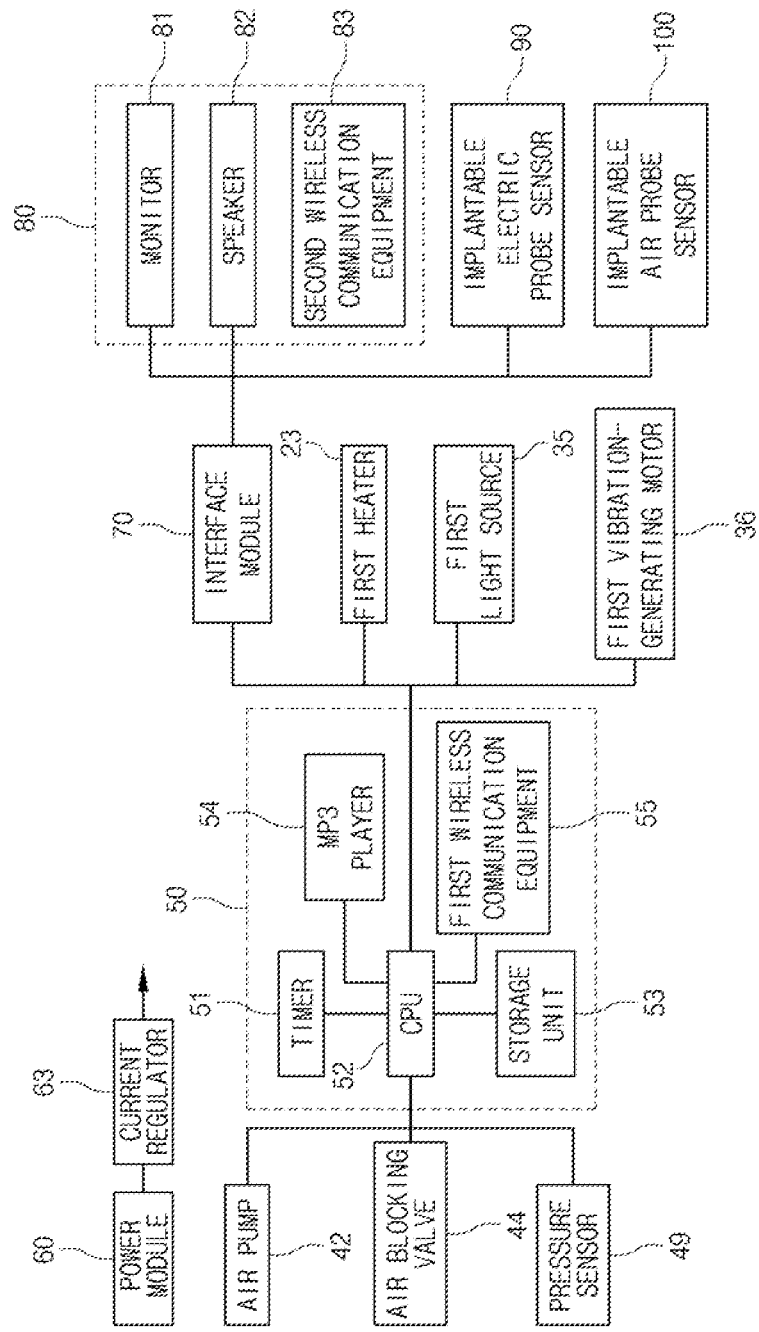
FIG. 5 illustrates a schematic block diagram showing the constitution of the seating apparatus for diagnosis and treatment of diagnosing and curing urinary incontinence, erectile dysfunction and defecation disorders according to the present invention.
Figure 6:
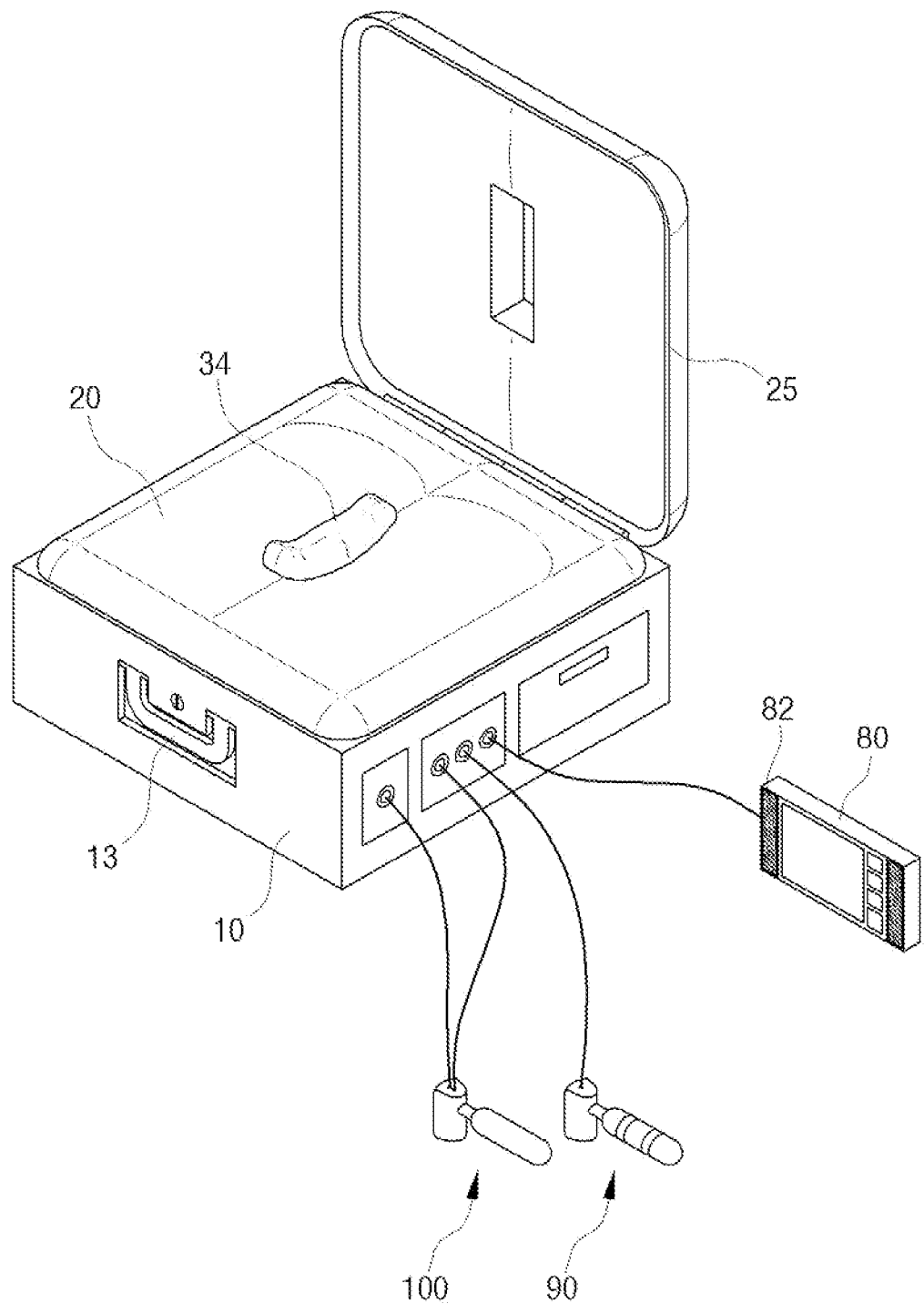
FIG. 6 illustrates a perspective diagram showing conditions for use of the seating apparatus for diagnosis and treatment of diagnosing and curing urinary incontinence, erectile dysfunction and defecation disorders according to the present invention.

FIG. 1 illustrates a perspective diagram showing a seating apparatus for diagnosis and treatment of diagnosing and curing urinary incontinence, erectile dysfunction and defecation disorders according to the present invention; FIG. 2 illustrates a sectional diagram A-A of FIG. 1; FIG. 3 illustrates a sectional diagram B-B of FIG. 1; FIG. 4 illustrates an exploded perspective diagram of the constitution of a contact-type air probe sensor module of the seating apparatus for diagnosis and treatment of diagnosing and curing urinary incontinence, erectile dysfunction and defecation disorders according to the present invention; and FIG. 5 illustrates a schematic block diagram showing the constitution of the seating apparatus for diagnosis and treatment of diagnosing and curing urinary incontinence, erectile dysfunction and defecation disorders according to the present invention.

Referring to FIGS. 1 to 5, a seating apparatus (1) for diagnosis and treatment of diagnosing and curing urinary incontinence, erectile dysfunction and defecation disorders according to the present invention consists of: a main case (10); a seat (20); a contact-type air probe sensor module (30); an air generation module (40); a control module (50); a power module (60); an interface module (70); a display module (80); an implantable electric probe sensor (90); and an implantable air probe sensor (100).

First, the main case (10) is composed of: a space (11), made up of durable synthetic resins or metal, wherein each component is installed inside for protection; a portable handle (13), installed in a front side and shaped like an open-top hexahedron; a support (15), installed at the bottom; and a storage groove for storing a display module (80), an implantable electric probe sensor (90) and an implantable air probe sensor (100), stated as below, to one side.

Further, the sear (20) includes a first heater (23) installed inside and combined to the top of the main case (10) in the manner of a typical structure with a through hole in the center; and a back (25) combined to be folded in the rear of the main case (10). Hereinafter, the back (25) may be utilized as a cover, and fixed by locking members (not illustrated) to the seat (20) or the main case (10) separately while moving. Here, it is desirable that the first heater (23) serves as hyperthermia of the underpart of a body while maintaining constant designated temperature automatically and is applied to a common wire-type resistance heater or a PTC (Positive Temperature Coefficient Resistance) film heater, which is an planar heating element. The PTC film heater is effective in preventing overheat due to short heating time (maximum), superior corrosion resistance and durability, semi-permanent lifespan, no short circuit by overheat, magnetic temperature control function and no separate on/off control function, and in emitting far infrared ray and minus ion with heat, necessary for hyperthermia.

Further, as illustrated in FIG. 4, the implantable air probe sensor module (30) consists of a frame (31), a lifting member (32), an air bag (33), a contact-type probe sensor (34), a first light source (35) and a first vibration-generating motor (36).

The frame (31), made up of synthetic resins or metal and shaped like a "凸"-figured open-top cylinder, forms a rectangle's first air tube hole (31a) to the side.

The lifting member (32), made up of synthetic resins or metal and shaped like a "冂"-figured open-top cylinder, forms a second air tube hole (32a) to the side and moves up and down in the frame (31).

Installed at the bottom of the lifting member (32) in the frame (31), the air bag (33) is expanded by air, supplied from an air generation module (40) stated below, thereby moving up the lifting member (32). Hereinafter, lifting motors and gears may be applied, instead of the air bag (33).

The contact-type probe sensor (34), made up of transparent or translucent elastic material (typical rubber, silicon rubber, soft plastic, etc.), functions as a sensor for human's movement in the state of right and left, up and down expansion by air while being shaped like longitudinally expanded hollow streamline for adhering to pelvic floor muscles, muscles of perineum and anal sphincters of a user upon expansion by air supplied from the air generation module (40); serves as strengthening (Kegel exercise) of pelvic floor muscles, muscles of perineum and anal sphincters by repeating expansion and contraction; and fixes the bottom by means of the top of the lifting member (32) and clamping rings (37). Hereinafter, it is desirable that the contact-type probe sensor (34) is configured to add Solitonium, which is a physiological active wave transmitting material, far infrared ray, tourmaline, which is a minus ion releasing material, elvan, etc.

It is desirable that the first light source (35) uses each or both of low level laser diode, which has output intensity of 5~50 mW and wavelength range of 630 nm-980 nm, or high luminance LED, which has output intensity of 5~50 mW and wavelength range of 420 nm-850 nm. If a low-energy laser beam which does not damage living cells is applied to body, physiological function of body is activated and nature healing power of an injured part is improved. Especially, if medical devices using laser are applied to blood vessels, prostate, reproductive organs, anus, and other injured parts of a patient, it is effective in clarifying blood, controlling internal immunity, and activating various enzymes. Therefore, laser treatment devices have been widely used in hospitals. It has been widely known that such low level laser influences microcirculation structures of blood flow, and human's blood flow. Besides, it is famous for acceleration of cell division, cell activation, immune cells, anti-inflammatory effects, and improvement of blood flow. Relevant clinical trials are completed. The wavelength of laser, used in therapy, is a wide range of visible rays, infrared rays, etc. Actually, effects and areas of each wavelength are different. In old days, laser medical equipment was mostly high level laser. Recently, Low Level Laser Therapy (LLLT) has been established, thereby performing active research and trial tests all over the world. The current treatment of various pain is the most prevalent in LLLT, obtaining large effects on the acupuncture points in the form of laser acupuncture by Canadian the Plugs Professor of He—Ne laser to remove pain. Now, it has been widely applied, because there are remarkable effects on removing pains as well as curing diseases by directly applying acupuncture to not only acupuncture points but also injured parts. Especially, low level laser is highly effective in all kinds of chronic diseases, conventionally known as incurable illness; patients have minor pain and side effects due to intemerate, nonsurgical and non medicated treatment; and medical expenses are much lower than those of traditional treatment.

Installed on one side of the lifting member (32), the first vibration-generating motor (36) shakes the contact-type probe sensor (34) by generating vibration. At this time, the first vibration-generating motor (36) may not be installed in case that a vibrator air pump is applied to an air pump (42) of the air generation module (40).

Further, the air generation module (40) consists of an air outlet (41), an air pump (42), a distribution terminal (43), an air blocking valve (44), first to fourth air tubes (45~48) and a pressure sensor (49).

Installed on one side of the main case (10), the air outlet (41) provides an implantable air probe sensor (100), as stated below.

It is desirable that the air pump (42) supplies air to the contact-type air probe sensor and the implantable air probe sensor, as stated below, and consists of a general air pump configured to output more than 800 mmHg of the maximum pressure or a vibrator air pump configured to generate vibration.

The distribution terminal (43) is shaped like a storage tank in which several exhaust pipes (43a), which connect to each of a first air tube (45), a second air tube (46) and a third air tube (47), are formed. The distribution terminal (43) distributes air, generated from the air pump (42), to the contact-type air probe sensor module (30) and the implantable air probe sensor (100).

The air blocking valve (44) expands, contracts and moves up and down the air probe sensor module (30) by emitting air toward outside or blocking air, and expands and contracts the implantable air probe sensor (100). Hereinafter, a direct current (DC)-normal-close type or direct current (DC)-normal-open type solenoid valve is applied to the air blocking valve (44).

The first air tube (45) is made up of flexible material like silicon in order to change a length in accordance with moving up and down of the lifting member (32) of the contact-type air probe sensor module (30), and expands the contact-type air probe sensor (34) by penetrating the first air tube hole (31a), formed in the frame (31) of the air blocking valve (44) and the contact-type air probe sensor module (30), and connecting to the second air tube hole (32a) of the lifting member (32).

The second air tube (46) is made up of flexible material like silicon, and expands the air bag (33) by penetrating the first air tube hole (31a), formed in the air blocking valve (44) and the frame (31) of the air probe sensor module (30), and connecting to the air bag (33).

The third air tube (47) is connected to the other side of the distribution terminal (43).

The fourth air tube (48) is interconnected to the air blocking valve (44) and the air outlet (41).

The pressure sensor (49) is connected to the other side of the third air tube (47), and outputs an input value by means of the control module (50) by measuring pressure with the electrically connected control module (50). At this time, it is desirable that the pressure sensor (49) refers to a digital pressure sensor, built in PCB with the control module (50), or a mechanic (Bellows type) pressure sensor, having pressure measurement range of more than 1~500 mmHg.

Furthermore, the control module (50) is configured to be fixed to the inside of the main case (10) while built in PCB; to control the whole of each component in accordance with control instruction inputted from the display module (80), as stated below; to measure contraction pressure and contraction duration of pelvic floor muscles (vagina muscles), muscles of perineum and anal sphincters for diagnosing urinary incontinence, erectile dysfunction and defecation disorders by using an input value, measured from the air generation module (40), and to supply these information to the display module (80); and to measure bio electrical impedance of pelvic floor muscles (vagina muscles) and anal sphincters by signals inputted from the implantable electric probe sensor (90), which is an external device, and to supply these information to the display module (80). Hereinafter, the control module (50) functions as strengthening (Kegel exercise) of pelvic floor muscles (vagina muscles), muscles of perineum and anal sphincters by repeating expansion and contraction of the contact-type air probe sensor module (30) and the implantable air probe sensor (100) in a regular pattern while controlling the air generation module (40). Hereinafter, it is desirable that the control module (50) includes a timer (51) for measuring time, a CPU (52), a storage unit (HDD, memory) (53), an MP3 player (54) and a first wireless communication equipment (55) for transmitting and receiving the display module (80) based on wireless data. Also, it is desirable to include music therapy while exercise and treatment, because an MP3 player provides functional music which is utilized in music therapy.

Meanwhile, the power module (60) is configured to form a power plug in the outer surface of the main case (10); to charge a battery (61) in the main case (10) with power source supplied from the power plug; to supply voltage, outputted from the battery (61), to each component; and to control the intensity of current, outputted from the battery (61) in accordance with regulation of the control module (50), throughout a current regulator (63). Hereinafter, it is desirable that the battery is a lithium-ion battery or a lithium-polymer batter, and the battery consists of a mass battery which enables to perform 20-cycle exercise with one charge.

Further, the interface module (70) is installed in the outer surface of the main case (10) with a plurality of terminals, and is electrically connected to the implantable electric probe sensor (90) and the implantable air probe sensor (100), which are external devices, by electrically connecting to the control module (50) and the power module (60).

Furthermore, the interface module (80) is configured to display all data, outputted from the control module (50), the implantable electric probe sensor (90), which is an external device, and the implantable air probe sensor (100), while accessing to the interface module (70) and electrically connecting to the control module (50) and the power module (60), and to transfer inputted control instruction to the control module (50). Hereinafter, the display module (80) refers to a common device such as terminals, to which a touch-type LCD is built, smartphones, tablet PCs, etc., and the display module (80) consists of a monitor (81) configured to output a button input means, which is operated by a user's instruction, and working situation on a screen, and a speaker (82) configured to output voice and music. Also, it is desirable that the display module (80) includes a second wireless communication equipment (83) configured to transmit and receive data, which enables to transmit and receive various data wirelessly, with the control module (50).

Figure 7:
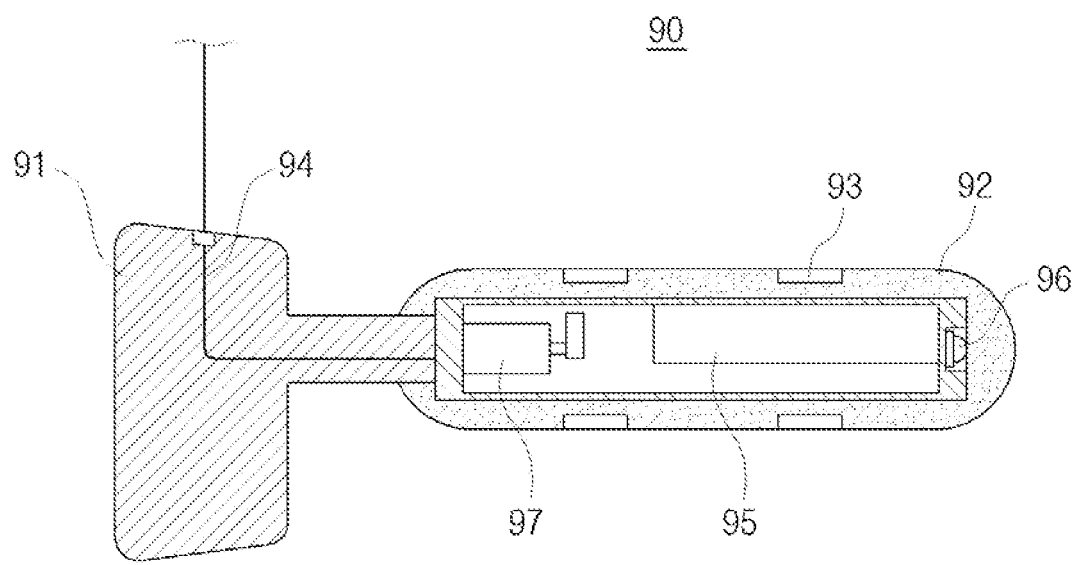
FIG. 7 illustrates a schematic sectional diagram showing the constitution of an implantable electric probe sensor of the seating apparatus for diagnosis and treatment of diagnosing and curing urinary incontinence, erectile dysfunction and defecation disorders according to the present invention.

Further, as illustrated in FIG. 7, the implantable electric probe sensor (90) is generally configured to form a plurality of ring-shaped electrodes (93) on the surface of a circular stick shaped first body (92), in which a first handle for grasping (91) is formed on end; to connect to the interface module (70) by expanding a first cable (94) in the first handle for grasping (91); to measure and output bio electrical impedance of pelvic floor muscles (vagina muscles) and anal sphincters of a user with the control module (50) for diagnosing urinary incontinence, erectile dysfunction and defecation disorders with power supplied from the power module (60); and to output current which enforces contraction and relaxation of pelvic floor muscles (vagina muscles) and anal sphincters of a user in accordance with regulation of the control module (50). At this time, the current intensity is regulated by the current regulator (63) of the power module (60). Hereinafter, the first body (92) may be made up of metal or PVC, PC, rubber, etc., and electrodes may be composed of metal or conductive plastic or conductive rubber. Also, the implantable electric probe sensor (90) further includes a second heater (95), which is a PTC heater element for generating heat; a second light source (96) configured to investigate light by using each or both of low level laser diode, which has output intensity of 5~50 mW and wavelength range of 630 nm~980 nm, or high luminance LED, which has output intensity of 5~50 mW and wavelength range of 420 nm~850 nm; and a second vibration-generating motor (97) configured to generate vibration.

Figure 8:
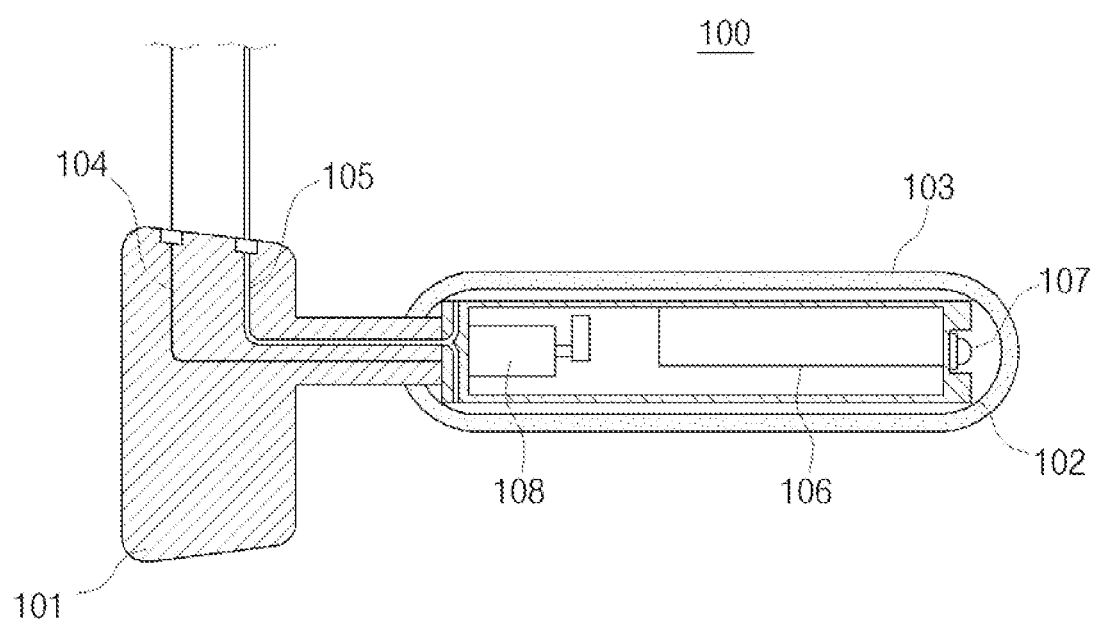
FIG. 8 illustrates a schematic sectional diagram showing the constitution of an implantable air probe sensor of the seating apparatus for diagnosis and treatment of diagnosing and curing urinary incontinence, erectile dysfunction and defecation disorders according to the present invention.

In addition, as illustrated in FIG. 8, the implantable air probe sensor (100), a well-known structure, is configured to function as accurate diagnose by injecting to human's vagina or anus and measuring contraction pressure and contraction duration of pelvic floor muscles and anal sphincters; to form a soft cover (103) in order to surround the surface of a circular stick shaped second body (102), in which a second handle for grasping (101) is formed on end for performing accurate diagnose and treatment more than the contact-type air probe sensor module (30) throughout biofeedback of strengthening (Kegel exercise) of pelvic floor muscles and anal sphincters; to connect to the interface module (70) by expanding a second cable (104) in the first handle for grasping (101); and combine to the air outlet (41) with a fifth air tube (105) expanded from the first handler for grasping (101). Hereinafter, the second body (102) is made up of metal or PVC, PC, rubber, etc., and the soft cover (103) is composed of rubber or silicon, urethane, soft plastic, etc. Also, the implantable air probe sensor (100) further includes a third heater (106), which is a PTC heater element for generating heat; a third light source (107) configured to investigate light by using each or both of low level laser diode, which has output intensity of 5~50 mW and wavelength range of 630 nm~980 nm, or high luminance LED, which has output intensity of 5~50 mW and wavelength range of 420 nm~850 nm; and a third vibration-generating motor (108) configured to generate vibration.

Accordingly, a seating apparatus (1) for diagnosis and treatment of diagnosing and curing urinary incontinence, erectile dysfunction and defecation disorders is characterized by comprising "Three ways-two channels system" configured to diagnose symptoms of urinary incontinence, erectile dysfunction and defecation disorders by selectively using the contact-type air probe sensor module (30), the implantable electric probe sensor (90), and the implantable air probe sensor (100) and to cure symptoms of urinary incontinence, erectile dysfunction and defecation disorders throughout biofeedback exercise and electrical stimulation by selectively using the contact-type air probe sensor module (30), the implantable electric probe sensor (90), and the implantable air probe sensor (100).

One way two channels—self-exam/measurement and self therapy/treatment by contact-type air probe sensor module (30)

Two ways two channels—self-exam/measurement and self therapy/treatment by implantable air probe sensor module (100)

Three ways two channels—self-exam/measurement and self therapy/treatment by implantable electric probe sensor module (90)

Hereinafter, the seating apparatus for diagnosis and treatment of diagnosing and curing urinary incontinence, erectile dysfunction and defecation disorders according to the present invention will be described in detail with the accompanying drawing.

Figure 9:
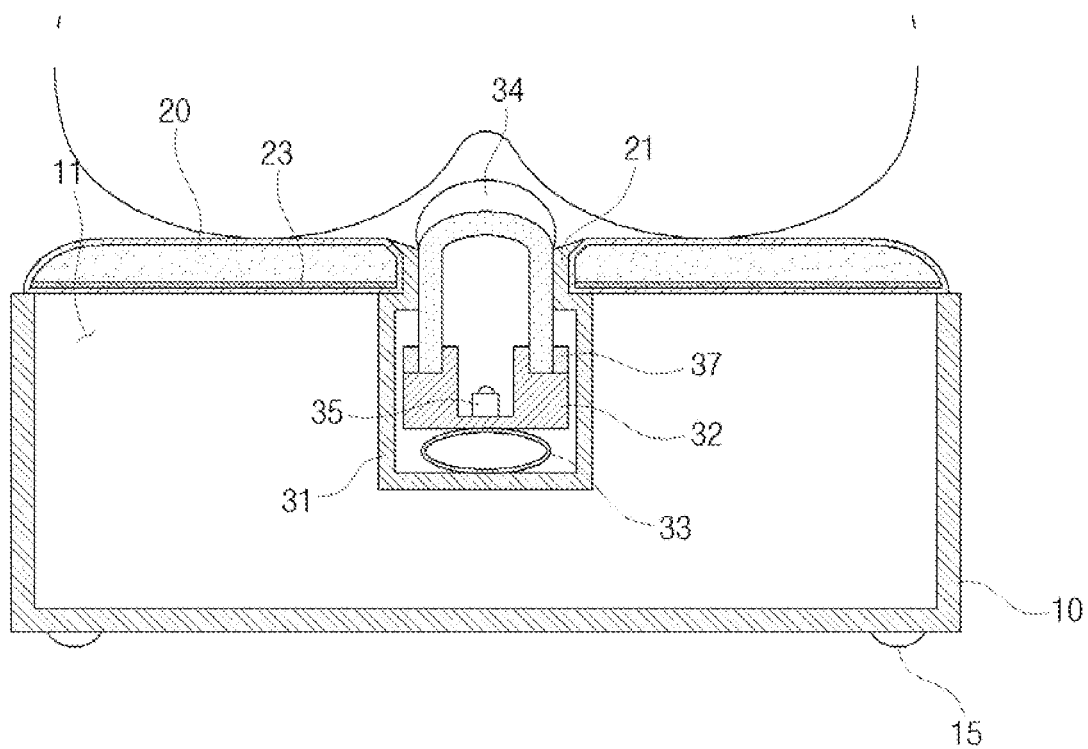
FIGS. 9 and 10 illustrate use state diagrams showing conditions for use of the seating apparatus for diagnosis and treatment of diagnosing and curing urinary incontinence, erectile dysfunction and defecation disorders according to the present invention.
Figure 10:
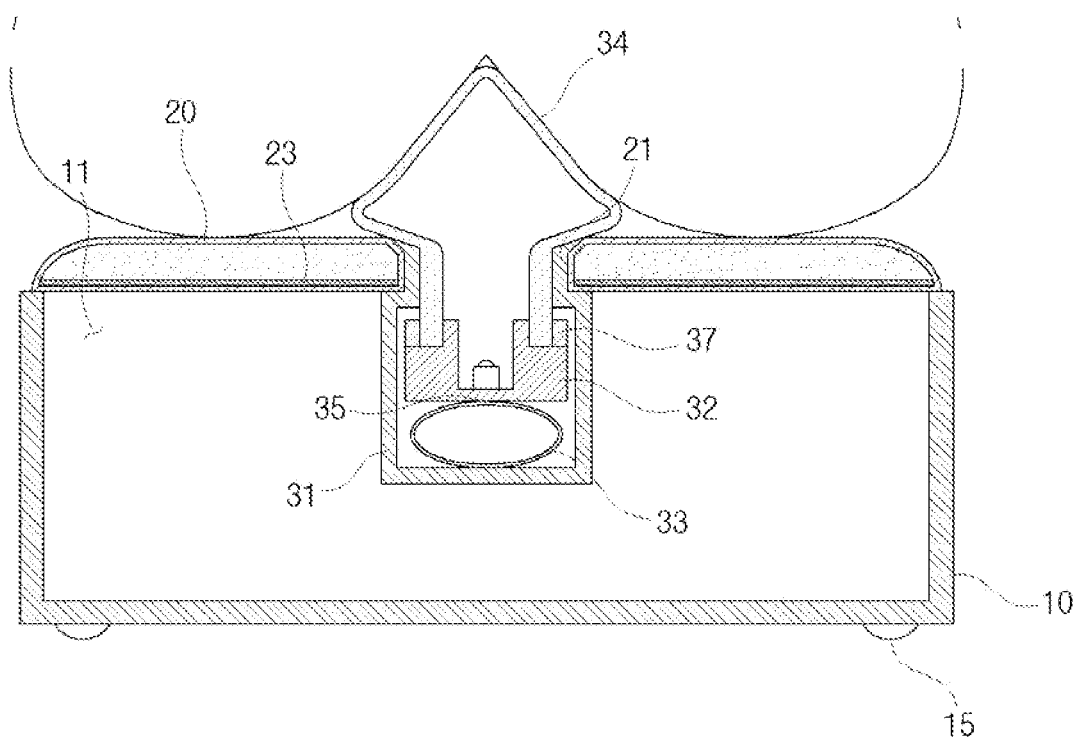

FIGS. 9 and 10 illustrate use state diagrams showing conditions for use of the seating apparatus for diagnosis and treatment of diagnosing and curing urinary incontinence, erectile dysfunction and defecation disorders according to the present invention.

On a basis of the stated constitution, three ways-two channels diagnosis and treatment of urinary incontinence, erectile dysfunction and defecation disorders are shown as below.

1. Operation of Contact-Type Air Probe Sensor Module (30)

1) Measurement of Contraction Pressure and Contraction Duration/Diagnosis

First, when booting up a system and pressing a seat-based measurement button of the display module (80) while accessing the display module (80) to the interface module (70), the air pump (42) of the air generation module (40) is operated, expanding the contact-type probe sensor (34) by air, which is supplied to the contact-type probe sensor (34) throughout the distribution terminal (43), the air blocking valve (44) and the first air tube (45).

Simultaneously, air expands the air bag (33) through the second air tube (46), thereby moving up the contact-type air probe sensor module (30) and sticking the contact-type probe sensor (34) to human body. At this time, the pressure sensor (49) detects adequate amount of air, which is inputted to the control module (50) in advance, to be injected to the contact-type probe sensor (34) and the air bag (33); and when adequate amount of air is injected, the air pump (42) stops operation of the control module (50) and the air blocking valve (44) is closed, thereby stopping air emitted.

In this condition, when a user contracts pelvic floor muscles (vagina muscles), muscles of perineum and anal sphincters as much as he can and keeps up its status for a long time, the pressure sensor (40) measures the maximum contraction pressure (mmHg) and the average contraction pressure of pelvic floor muscles, muscles of perineum and anal sphincters, and the control module (50) measures contraction duration by timing when the pressure value is down below to a constant value from the maximum point.

Then, the pressure sensor (49) measures resting pressure (mmHg) of pelvic floor muscles, muscles of perineum and anal sphincters when pelvic floor muscles (vagina muscles), muscles of perineum and anal sphincters are not under strain, that is, muscles are relaxed.

After repeating and measuring the above motions, the control module (50) outputs the measured maximum value, the minimum value and the average value in the manner of screen and voice throughout the display module (80) and stores in a storage unit.

2) Feedback Exercise (Kegel Exercise)/Treatment

First, when booting up a system and pressing a seat-based measurement button of the display module (80) while accessing the display module (80) to the interface module (70), the air pump (42) of the air generation module (40) is operated, expanding the contact-type probe sensor (34) by air, which is supplied to the contact-type probe sensor (34) throughout the distribution terminal (43), the air blocking valve (44) and the first air tube (45). At this time, the pressure sensor (49) detects adequate amount of air to be injected to the contact-type probe sensor (34) and the air bag (33) in accordance with a user's step therapy pattern (exercise level), which is inputted to the control module (50) in advance; and when adequate amount of air is injected, the air pump (42) stops operation of the control module (50) and the air blocking valve (44) is closed, thereby stopping air emitted.

Further, when a user performs feedback (biofeedback, exercise for strengthening pelvis) for repeating contraction and relaxation of muscles in compliance with instruction in the manner of screen and voice from the display module (80), the pressure sensor (49) measures contraction pressure, contraction duration and resting pressure of pelvic floor muscles (vagina muscles), muscles of perineum and anal sphincters by catching movements of pelvic floor muscles, muscles of perineum and anal sphincters of human body by means of the contact-type probe sensor (34).

Furthermore, the control module (50) may display exercise data or instruction or guiding lines in the manner of bar graphs, numbers or animation throughout screens of the display module (80), and output voice or melody throughout speakers. Also, by pressing option buttons of the display module (80) in order, a user selects vibration, heating and beam therapy functions, and the selected function runs during treatment when pressing a start button.

2. Operation of Implantable Air Probe Sensor (100)

1) Measurement of Contraction Pressure and Contraction Duration/Diagnosis

First, when booting up a system, accessing the display module (80) and the implantable air probe sensor (100) to the interface module (70), injecting the implantable air probe sensor (100) to coelom of a user while combining the expansion tube (105) to the air outlet (41) of the air generation module (40), and pressing an injection-based measurement button of the display module (80), the air pump (42) of the air generation module (40) is operated, expanding the soft cover (103) of the implantable air probe sensor (100) by air, which is supplied to the implantable air probe sensor (100) throughout the distribution terminal (43), the air blocking valve (44) and the fourth air tube (48). At this time, the pressure sensor (49) detects adequate amount of air, which is inputted to the control module (50) in advance, to be injected to the implantable air probe sensor (100); and when adequate amount of air is injected, the air pump (42) stops operation of the control module (50) and the air blocking valve (44) is closed, thereby stopping air emitted.

In this condition, when a user contracts pelvic floor muscles (vagina muscles) and anal sphincters as much as he can and keeps up its status for a long time, the pressure sensor (40) measures the maximum contraction pressure (mmHg) and the average contraction pressure of pelvic floor muscles (vagina muscles) and anal sphincters, and the control module (50) measures contraction duration by timing when the pressure value is down below to a constant value from the maximum point.

Then, the pressure sensor (49) measures resting pressure (mmHg) of pelvic floor muscles (vagina muscles) and anal sphincters when pelvic floor muscles (vagina muscles) and anal sphincters are not under strain, that is, muscles are relaxed.

After repeating and measuring the above motions, the control module (50) outputs the measured maximum value, the minimum value and the average value in the manner of screen and voice throughout the display module (80) and stores in a storage unit.

2) Feedback Exercise (Kegel Exercise)/Treatment

First, when booting up a system, accessing the display module (80) and the implantable air probe sensor (100) to the interface module (70), injecting the implantable air probe sensor (100) to coelom of a user while combining the soft cover (103) to the air outlet (41) of the air generation module (40), and pressing an injection-based exercise button of the display module (80), the air pump (42) of the air generation module (40) is operated, expanding the soft cover (103) of the implantable air probe sensor (100) by air, which is supplied to the implantable air probe sensor (100) throughout the distribution terminal (43), the air blocking valve (44) and the fourth air tube (48). At this time, the pressure sensor (49) detects adequate amount of air to be injected to the implantable air probe sensor (100) in accordance with a user's step therapy pattern (exercise level), which is inputted to the control module (50) in advance; and when adequate amount of air is injected, the air pump (42) stops operation of the control module (50) and the air blocking valve (44) is closed, thereby stopping air emitted.

Further, when a user performs feedback (biofeedback, exercise for strengthening pelvis) for repeating contraction and relaxation of muscles in compliance with instruction in the manner of screen and voice from the display module (80), the pressure sensor (49) measures contraction pressure, contraction duration and resting pressure of pelvic floor muscles (vagina muscles) and anal sphincters by catching movements of pelvic floor muscles (vagina muscles) and anal sphincters of human body by means of the implantable air probe sensor (100).

Furthermore, the control module (50) may display exercise data or instruction or guiding lines in the manner of bar graphs, numbers or animation throughout screens of the display module (80), and output voice or melody throughout speakers. Also, by pressing option buttons of the display module (80) in order, a user selects vibration, heating and beam therapy functions, and the selected function runs during treatment when pressing a start button.

3. Operation of Implantable Electric Probe Sensor (90)

1) Measurement of Bio Electrical Impedance/Diagnosis

First, when booting up a system, accessing the display module (80) and the implantable electric probe sensor (90) to the interface module (70), and pressing an injection-based impedance measurement button of the display module (80) while injecting the implantable electric probe sensor (90) to coelom of a user, the bio electrical impedance of pelvic floor muscles (vagina muscles) and anal sphincters of a user is measured by electrodes (90) and is outputted throughout the control module (50). At this time, the current intensity is regulated by the current regulator (63) of the power module (60).

Then, the control module (50) outputs the measured bio electrical impedance in the manner of screen and voice throughout the display module (80) and stores in a storage unit.

2) Treatment

First, when booting up a system, accessing the display module (80) and the electric probe sensor (90) to the interface module (70), pressing an electrical treatment button of the display module (80) while injecting the implantable electric probe sensor (90) to coelom of a user, and pressing a level selection button in accordance with a user's step therapy pattern (exercise level), which is inputted to the control module (50) in advance, moderate-intensity micro current from the current regulator (63) of the power module (60) is applied to the electrodes (93) of the implantable electric probe sensor (90), injected to human's coelom, during predetermined therapy time. Then, urinary incontinence, erectile dysfunction of pelvic floor muscles (vagina muscles) and anal sphincters are cured by repeating compulsory contraction and relaxation throughout low frequency current.

Furthermore, the control module (50) may display treatment level, current intensity and residual time for treatment in the manner of bar graphs, numbers or animation throughout screens of the display module (80), and output voice or melody throughout speakers. Also, by pressing option buttons of the display module (80) in order, a user selects vibration, heating and beam therapy functions, and the selected function runs during treatment when pressing a start button.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A seating apparatus for diagnosis and treatment of urinary incontinence, erectile dysfunction and defecation disorders comprising:

a main case equipped with a space inside and shaped in the form of an open-top hexahedron;

a seat configured to connect to the upper side of the main case and to form a through hole at the center thereof;

a contact-type air probe sensor module configured to be housed within the main case by penetrating the through hole of the seat to make the top of the contact-type air probe sensor module protrude toward the upper side of the seat, the contact-type air probe sensor module being configured to measure contraction pressure and contraction duration of pelvic floor muscles, muscles of the perineum and anal sphincters of a user while the contact-type air probe sensor module being moved up and down and expanded by air, and the contact-type air probe sensor module being configured to induce contraction and relaxation of the user;

an air generation module, equipped with an air outlet, wherein the air generation module is configured to be fixed to the inside of the main case and to supply air to the contact-type air probe sensor module;

an implantable air probe sensor connected to the air outlet of the air generation module, a control module configured to be fixed to the inside of the main case, to control the apparatus in accordance with a control instruction to measure contraction pressure and contraction duration of pelvic floor muscles, muscles of perineum and anal sphincters for obtaining and outputting first values measured by the apparatus in order to diagnose urinary incontinence, erectile dysfunction and defecation disorders by using an input value, measured from the air generation module, and control the apparatus to measure bio-electrical impedance of pelvic floor muscles and anal sphincters on a basis of signals for obtaining and outputting second values measured by the apparatus;

an implantable electric probe sensor inputting the signals to the control module;

a power module, said power module equipped with a power plug to the outer surface of the main case, wherein the power module is configured to charge a battery in the main case with power source supplied from the power plug, wherein the power module is configured to supply voltage outputted from the battery, and wherein the power module is configured to control intensity of electric current outputted from the battery in accordance with external control;

an interface module, which is installed to the outer surface of the main case and is configured to connect to the implantable electric probe sensor and the implantable air probe sensor by electrically combining the control module and the power module; and and a display module, said display module configured to display the first and second values outputted from said control module and said implantable electric probe sensor and the implantable air probe sensor by electrically connecting to said control module and the power module while accessing said interface module, and to transfer the inputted control instruction to said control module, wherein the contact-type air probe sensor module comprises:

a frame, shaped in the form of an "凸"-figured open-top cylinder, configured to form a rectangle's first air tube hole to the side;

a lifting member, shaped in the form of an "凸"-figured open-top cylinder, configured to form a second air tube hole to the side and to move up and down in the frame;

an air bag, installed at the bottom of the lifting member in the frame, configured to be expanded by air, supplied from the air generation module, and to move up the lifting member; and a contact-type probe sensor, made up of transparent or translucent elastic material, configured to be the form of streamline for adhering to pelvic floor muscles, muscles of perineum and anal sphincters of a user upon expansion by air supplied from the air generation module, and to fix the bottom by means of the top of the lifting member and clamping rings.

2. The apparatus according to claim 1, wherein the implantable electric probe sensor is configured to connect to the interface module, to be outputted by the control module with measured bio-electrical impedance of pelvic floor muscles and anal sphincters of a user for diagnosing urinary incontinence and erectile dysfunction with power source of the power module, and to output current which enforces contraction and relaxation of pelvic floor muscles and anal sphincters of a user in accordance with regulation of the control module.

3. The apparatus according to claim 1, wherein the implantable air probe sensor is configured to mechanically combine with the air outlet of the air generation module, to measure contraction pressure and contraction duration of pelvic floor muscles and anal sphincters of a user by being expanded by air while accessing to the interface module, and to induce contraction and relaxation.

4. The apparatus according to claim 1, wherein said main case, made up of synthetic resins or metal, comprises a handle in a front side thereof, a support at the bottom thereof, and a storage groove for storing the display module, the implantable electric probe sensor and the implantable air probe sensor to one side thereof.

5. The apparatus according to claim 1, wherein the seat further includes a heater installed inside said main case; and a back configured to be folded in the rear of the main case.

6. The apparatus according to claim 1, wherein said contact-type air probe sensor module further includes:

a light source, installed inside of said lifting member, configured to generate light for activating a physiological function of a body of the user; and a vibration-generating motor, installed in one side of said lifting member, configured to generate vibration.

7. The apparatus according to claim 1, wherein the air generation module comprises:

an air pump configured to generate air; a distribution terminal configured to distribute air generated from the air pump;

an air blocking valve configured to connect to one side of the distribution terminal;

a first air tube, made up of flexible material, configured to expand the contact-type probe sensor by penetrating an air tube hole formed in the air blocking valve and the frame of the contact-type air probe sensor module and combining to the second air tube hole of the lifting member;

a second air tube, made up of flexible material, configured to expand the air bag by penetrating the air tube hole formed in the air blocking valve and the frame of the contact-type air probe sensor module and combining to the air bag;

a third air tube connected to one side of the distribution terminal;

a fourth air tube configured to interconnecting the air blocking valve and the air outlet; and a pressure sensor configured to connect to one end of the third air tube, and to output an input value by means of the control module with measured pressure which is electrically connected to the control module.

8. The apparatus according to claim 3, wherein the implantable electric probe sensor further includes:

a heater configured to generate heat;

a light source configured to generate light for activating a physiological function of a body of the user; and a vibration-generating motor configured to generate vibration.

9. The apparatus according to claim 1, wherein the control module further includes a first wireless communication equipment configured to communicate with the display module based on wireless data, and wherein said display module further includes a second wireless communication equipment configured to communicate with the control module based on wireless data.

* * * * *